US012778509B2

(12) United States Patent
Gross

(10) Patent No.: US 12,778,509 B2
(45) Date of Patent: Nov. 3, 2026

(54) APPARATUSES AND SYSTEMS FOR MONITORING WOUND CLOSURE AND DELIVERING LOCAL TREATMENT AGENTS

(71) Applicant: Michael Gross, Halifax (CA)

(72) Inventor: Michael Gross, Halifax (CA)

(73) Assignee: Inkwell Health Ltd., Ontario (CA)

( * ) Notice: Subject to any disclaimer, the term of this patent is extended or adjusted under 35 U.S.C. 154(b) by 1161 days.

(21) Appl. No.: 16/960,121

(22) PCT Filed: Jan. 9, 2019

(86) PCT No.: PCT/CA2019/050032

§ 371 (c)(1),
(2) Date: Jul. 6, 2020

(87) PCT Pub. No.: WO2019/136559

PCT Pub. Date: Jul. 18, 2019

(65) Prior Publication Data

US 2021/0069390 A1 Mar. 11, 2021

Related U.S. Application Data

(60) Provisional application No. 62/615,178, filed on Jan. 9, 2018.

(51) Int. Cl.
*A61B 5/00* (2006.01)
*A61B 5/107* (2006.01)
(Continued)

(52) U.S. Cl.
CPC .......... *A61B 5/6833* (2013.01); *A61B 5/0077* (2013.01); *A61B 5/1073* (2013.01);
(Continued)

(58) Field of Classification Search
CPC ................ A61B 5/6833; A61B 5/0077; A61B 5/1073; A61B 5/1079; A61B 5/445;
(Continued)

(56) References Cited

U.S. PATENT DOCUMENTS 3,613,679 A 10/1971 Bijou
4,390,442 A * 6/1983 Quick ...................... A61K 8/34 510/480

(Continued)

FOREIGN PATENT DOCUMENTS

CN 1089168 A 7/1993
CN 104620088 A 5/2015

(Continued)

OTHER PUBLICATIONS

A.C. Williams and B.W. Barry, Penetration enhancers, Oct. 13, 2003, Advanced Drug Delivery Reviews, 56, 603-618 (Year: 2003).*

(Continued)

*Primary Examiner* — Philip R Wiest
*Assistant Examiner* — Peter Daniel Smith
(74) *Attorney, Agent, or Firm* — Smart & Biggar LP

(57) ABSTRACT

Systems and methods for monitoring wound closure are described herein. The systems include a dressing for applying to a wound. The dressing includes an elasticized membrane having a first side and a second side and a reference object disposed on the first side. The elasticized membrane is movable between a relaxed state where the reference object has a first configuration and a stretched state where the reference object has a second configuration, the second configuration corresponding to an amount of swelling of an area of skin around the wound. The systems also include a camera for capturing an image of the reference object in the second configuration and a processor for comparing the image to a stored image of the reference object in the first
(Continued)

configuration and determining a degree of swelling of the area of skin around the wound based on the comparison.

8 Claims, 14 Drawing Sheets

(51) Int. Cl.
*A61F 13/00* (2024.01)
*A61F 13/05* (2024.01)

(52) U.S. Cl.
CPC ............ *A61B 5/1079* (2013.01); *A61B 5/445* (2013.01); *A61B 5/4878* (2013.01); *A61F 13/00059* (2013.01); *A61F 13/00063* (2013.01); *A61F 2013/0094* (2013.01); *A61F 13/05* (2024.01)

(58) Field of Classification Search
CPC ............ A61B 5/4878; A61F 13/00059; A61F 13/00063; A61F 13/00068; A61F 2013/0094; A61K 9/7092
See application file for complete search history.

(56) References Cited

U.S. PATENT DOCUMENTS

| | | | | |
|---|---|---|---|---|
| 5,462,743 | A | 10/1995 | Turner et al. | |
| 7,854,716 | B2 * | 12/2010 | Schuren | A61F 13/08 602/53 |
| 2003/0135171 | A1 * | 7/2003 | Ingram | A61F 13/107 604/308 |
| 2005/0118246 | A1 * | 6/2005 | Wong | A61K 9/0065 424/449 |
| 2007/0209447 | A1 * | 9/2007 | Christ, Jr. | G01L 1/247 73/800 |
| 2013/0060209 | A1 * | 3/2013 | Tyler | A61F 13/025 604/307 |
| 2013/0131565 | A1 * | 5/2013 | Dallafior | A61F 5/01 602/5 |
| 2013/0190655 | A1 * | 7/2013 | Jackson | A61B 5/442 600/587 |
| 2013/0335545 | A1 | 12/2013 | Darling | |
| 2015/0154451 | A1 * | 6/2015 | Liu | G06T 7/0014 382/111 |
| 2016/0252346 | A1 * | 9/2016 | Bismuth | H04N 23/64 356/610 |
| 2016/0331461 | A1 | 11/2016 | Cheatham et al. | |
| 2017/0266370 | A1 * | 9/2017 | Cerman | A61M 5/158 |
| 2018/0092944 | A1 * | 4/2018 | Kim | A61K 45/06 |

FOREIGN PATENT DOCUMENTS

| | | | |
|---|---|---|---|
| JP | 2015534039 | | 11/2015 |
| WO | 9409848 | A1 | 5/1994 |
| WO | 2014014672 | A1 | 1/2014 |
| WO | 2014121435 | A1 | 8/2014 |
| WO | 2017121424 | A1 | 1/2017 |
| WO | 2017121434 | A1 | 7/2017 |
| WO | 2017121435 | A1 | 7/2017 |

OTHER PUBLICATIONS

International Search Report and Written Opinion of corresponding International Patent Application No. PCT/CA2019/050032 dated Apr. 9, 2019, 15 pages.
Supplementary European Search Report of corresponding European Patent Application No. EP19738907 dated Feb. 4, 2021, 13 pages.
Supplementary Partial European Search Report of corresponding European Patent Application No. EP19738907 dated Nov. 13, 2020, 13 pages.
Adrian C. Williams, Penetration enhancers, Oct. 13, 2003, West Yorkshire, UK.
Examination Report No. 1 for standard patent application, Australian Government, IP Australia, Nov. 5, 2023.
Examination Report, European Patent Office, Nov. 27, 2023.
Notice of Preliminary Rejection, Korean Intellectual Property Office, Nov. 8, 2023.
Substantive Report, Saudi Authority for Intellectual Property, Jan. 31, 2023.

* cited by examiner

APPARATUSES AND SYSTEMS FOR MONITORING WOUND CLOSURE AND DELIVERING LOCAL TREATMENT AGENTS

This application is a National Stage of co-pending International Application No. PCT/CA2019/050032 filed on Jan. 9, 2019 which claims the benefit of United Stated Provisional Application Ser. No. 62/615,178 filed Jan. 9, 2018, each of which is hereby incorporated herein by reference.

TECHNICAL FIELD

The embodiments disclosed herein relate to apparatuses and systems for wound closure, and, in particular to medical strips and wound dressings as components of systems for monitoring wound closure, while delivering agents to improve analgesia and reduce swelling to the skin.

BACKGROUND

Skin provides a protective barrier against foreign materials and infection. The epidermis is the outer of the two layers that make up the skin, the inner layer being the dermis. When a wound or a surgical incision in the skin is repaired, the purpose of the repair is to keep the edges of the epidermis together so that natural healing can take place. Traditional methods of keeping the edges of the epidermis together include the use of sutures, staples and adhesive tapes. After a wound heals, these devices are removed from the epidermis, usually by a medical practitioner, nurse or doctor. The removal of these devices can result in pain to the patient and/or holes in the skin that can become infected and/or bleed and require a subsequent protective dressing.

Wound healing involves a multitude of different responses from the human body. Briefly, in the first 24 hours of wound healing, there is an increase of blood supply to the area of the wound and an increase in the amount of other fluid via the blood to the tissues surrounding the wound, so called oedema or swelling. This influx of fluid to the area of the wound causes redness and swelling of the wound and the surrounding areas. Further, secreted factors also move towards the area around the wound, which causes more swelling and more blood supply to the area of the wound. These factors can be controlled with the use of anti-inflammatory agents, traditionally provided to the patient either by mouth or intravenously post-surgery. The swelling and wound response stimulates pain receptors in the dermis and this causes the patient pain. Pain can and is usually treated with a combination of oral and intravenous agents such as morphine.

Excessive wound swelling by itself can be very painful and cause discomfort to the patient and in certain cases can be dangerous, such as in head and neck surgery. Excessive wound swelling can also indicate that there is a wound infection within the wound that is not obvious to the patient. The degree of swelling of a wound can sometimes alert the attending medical practitioner as to the presence or likelihood of an infection. However, most patients are not able to make that determination about the likelihood of infection based on degree of swelling alone. Accordingly, patients typically visit physicians unnecessarily for a normal degree of wound swelling and often too late for a large degree of swelling when infection is already established within the wound.

Accordingly, there is a need for apparatuses and systems for monitoring wound closure and delivering local treatment agents.

SUMMARY

The present disclosure describes apparatuses and systems for monitoring wound closure. The apparatuses and systems gather data of relevance to a medical professional and to a patient and present that data to the medical professional and the patient to improve post-application monitoring of wounds.

The apparatuses and systems described herein generally include a dressing and a temperature indicating strip. The dressing may be applied across a wound and can provide for measuring an amount of swelling of skin around the wound during the healing process. The dressing may also deliver analgesics and anti-inflammatory agents to the skin around the wound, for example to an area of skin adjacent to the wound, to facilitate healing and pain control.

The apparatuses and systems described herein generally include a temperature-indicating strip that runs along the wound, collects fluids to a closed container and also provides a visual measurement of the temperature of the underlying skin.

The apparatuses and systems described herein generally provide feedback regarding the amount of swelling of the skin around the wound and other general wound health information to medical professionals including measurements of changes in the expansion of two planes of an elasticized membrane of the dressing applied to the wound. This system is based on images captured by the patient with, for example, a cell phone camera and a mobile application or program that controls the camera so that the operator of the cell phone camera is enabled to take an appropriate image for measurement by the application. Measurement algorithms associated with the mobile application can analyze the data, and images obtained by the application to establish a degree of wound change in terms of swelling and temperature. When those changes exceed preset guidelines, for example, a notification can be sent to the medical professional responsible and to the patient (e.g. their physician).

The apparatuses and systems described herein provide for measuring swelling and administering analgesics and anti-inflammatory agents to the wound and therefore may enhance the wound healing experience for the patient and the medical professional alike. As described above, an application may be used to provide images showing swelling of the wound. The application can measure the degree of swelling precisely based on markings on the dressing and send the measurements to the medical professional through one or more means (e.g. email, mobile or desktop application). A temperature-indicating strip may also be used to provide data to a medical professional to assess the wound (e.g. for indications of infection through increased temperature). Further, the temperature-indicating strip may provide for collecting discharge of fluid or blood from the wound in a closed-system that is painless for the patient and aesthetic as it may not require changing of soaked dressings and it prevents fluids affecting clothing.

In one aspect, a system for monitoring wound closure is provided. The system includes a dressing for applying to the wound including an elasticized membrane having a first side and a second side and a reference object disposed on the first side of the elasticized membrane. The elasticized membrane is movable between a relaxed state where the reference object has a first configuration and a stretched state where the reference object has a second configuration. The second configuration of the reference object corresponds to an amount of swelling of an area of skin around the wound. The system also includes a camera for capturing an image of the reference object in the second configuration and a processor for comparing the image of the reference object in the second configuration to a stored image of the reference object in the first configuration and determining a degree of swelling of the area of skin around the wound based on the comparison.

In some other embodiments, the processor is remotely located and the camera further comprises a transmitter for transmitting the image to the processor over a network.

In some other embodiments, the camera and the processor are part of a computing device.

In some other embodiments, the dressing further comprises at least one container coupled to the second side of the elasticized membrane, the at least one container having a first end sealingly coupled to the elasticized membrane, a second end spaced from the first end defining an opening of the container, and a continuous wall between the first end and the second end defining a volume of the container.

In some other embodiments, the reference object is a reticule having a series of lines or fibres.

In another aspect, a dressing for applying to a wound is provided. The dressing includes an elasticized membrane having a first side and a second side and a reference object disposed on the second side of the elasticized membrane. The elasticized membrane is movable between a relaxed state where the reference object has a first configuration and a stretched state where the reference object has a second configuration. The second configuration of the reference object corresponds to an amount of swelling of an area of skin around the wound.

In some other embodiments, the dressing includes at least one container coupled to the second side of the elasticized membrane, the at least one container having a first end sealingly coupled to the elasticized membrane, a second end spaced from the first end defining an opening of the container, and a continuous wall between the first end and the second end defining a volume of the container.

In some other embodiments, the container comprises an adhesive disposed on the second end of the container to removably attach the dressing to an area of skin around the wound.

In some other embodiments, the dressing includes a plurality of containers aligned between a first end and a second end of the elasticized membrane.

In some other embodiments, the container is made of a foam-based material.

In some other embodiments, the container has a circular shape and a height of 2 to 3 mm.

In some other embodiments, the container comprises a medicament disposed in the volume of the container to be delivered to the wound when the dressing is applied to the wound.

In some other embodiments, the medicament of the container comprises a long acting analgesic drug, an anti-inflammatory drug and/or comprises an emollient designed to restore skin smoothness.

In some other embodiments, the medicament comprises a layer of a long acting analgesic drug positioned adjacent to the second end of the container, a layer of an emollient designed to restore skin smoothness at the first end of the container and a layer of an anti-inflammatory gel therebetween.

In some other embodiments, the reference object is a reticule having a series of lines or fibres.

In some other embodiments, the dressing includes a second membrane releasably coupled to the second end of the at least one container via an attachment component.

In another aspect, a dressing for applying to a wound is provided. The dressing includes an elasticized membrane having a first side and a second side and at least one container coupled to the second side of the elasticized membrane, the at least one container having a first end sealingly coupled to the elasticized membrane, a second end spaced from the first end defining an opening of the container, and a continuous wall between the first end and the second end defining a volume of the container.

In another aspect, a temperature-indicating strip for applying to a wound is provided. The temperature indicating strip includes a temperature-indicating membrane having a first end spaced apart from a second end and a first side and a second side, the first side of the membrane configured to indicate a temperature of an area of skin around the wound, and at least one tube coupled to the second side of the temperature-indicating membrane extending between the first end and the second end, the at least one tube configured to gather fluid draining from the wound.

In some other embodiments, the temperature-indicating membrane is an elastic-based membrane.

In some other embodiments, liquid crystals of the temperature-indicating membrane indicate the temperature of the area of skin around the wound.

In some other embodiments, the at least one tube is configured to fluidly couple to a device that collects fluid gathered by the at least one tube to form a closed system.

In another aspect, a computer-implemented method of monitoring wound closure is provided. The computer implemented method includes: receiving from a patient device image data representative of a dressing applied to the wound, the dressing movable between a first configuration and a second configuration, the second configuration indicating a degree of swelling of the wound; calculating the degree of swelling of the wound based on the image data received from the patient device; and transmitting the degree of swelling and the image data to a physician device for assessment.

In another aspect, a system for monitoring wound closure is provided. The system includes a computer processor coupled to a memory, wherein the computer processor is programmed to monitor closure of the wound by: receiving from a patient device image data representative of a dressing applied to the wound, the dressing movable between a first configuration and a second configuration, the second configuration indicating a degree of swelling of the wound; calculating the degree of swelling of the wound based on the image data received from the patient device; and transmitting the degree of swelling and the image date to a physician device for assessment.

In another aspect, a system for monitoring swelling of a part of a body is provided. The system includes a dressing for applying to the part of the body, the dressing comprising an elasticized membrane having a first side and a second side; and a reference object disposed on the first side of the elasticized membrane; wherein the elasticized membrane is movable between a relaxed state where the reference object has a first configuration and a stretched state where the reference object has a second configuration, the second configuration of the reference object corresponding to an amount of swelling of the part of the body; a first device having a camera for capturing an image of the reference object in the second configuration; and a second device configured to: receive the image of the reference object from the first device, and determine a degree of swelling of the part of the body underlying the dressing.

In another aspect, a dressing for applying to a part of a body is provided. The dressing includes an elasticized membrane having a first side and a second side; and a reference object disposed on the first side of the elasticized membrane; wherein the elasticized membrane is movable between a relaxed state where the reference object has a first configuration and a stretched state where the reference object has a second configuration, the second configuration of the reference object corresponding to an amount of swelling of the part of the body.

In some other embodiments, the reference object includes markings and a position of the markings relative to the part of the body when the reference object has the first configuration is different than the position of the markings relative to the part of the body when the reference object has the second configuration.

Other aspects and features will become apparent, to those ordinarily skilled in the art, upon review of the following description of some exemplary embodiments.

BRIEF DESCRIPTION OF THE DRAWINGS

The drawings included herewith are for illustrating various examples of articles, methods, and apparatuses of the present specification. In the drawings.

DETAILED DESCRIPTION

Figure 1:
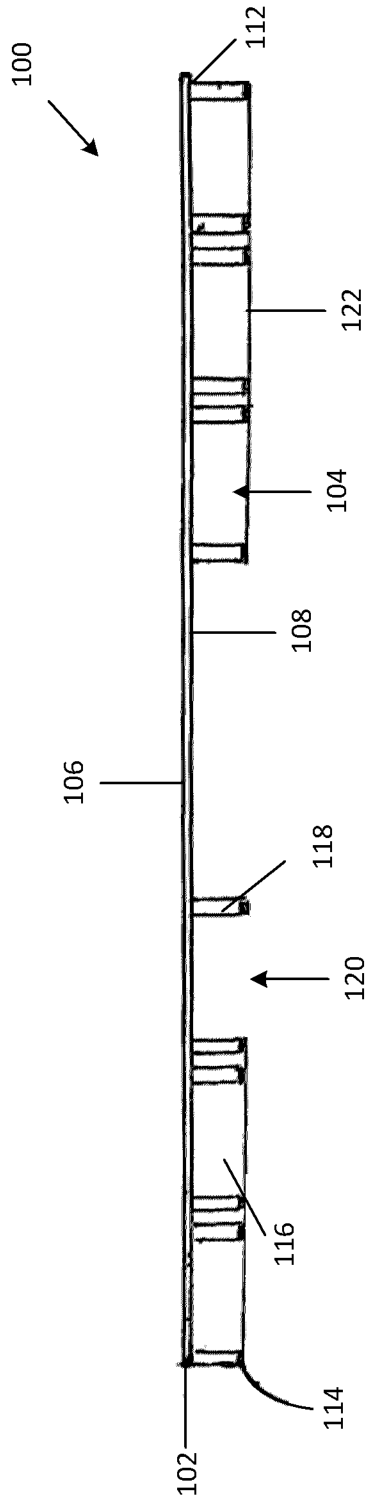
FIG. 1 is an end view of a dressing for applying to a wound, according to one embodiment.

Various apparatuses, systems and methods will be described below to provide an example of each claimed embodiment. No embodiment described below limits any claimed embodiment and any claimed embodiment may cover apparatuses, systems and methods that differ from those described below. The claimed embodiments are not limited to apparatuses, systems and methods having all of the features of any one apparatus, system or method described below or to features common to multiple or all of the apparatuses, systems and methods described below.

The embodiments described herein are implemented as apparatuses, systems and methods for monitoring a wound and transmitting data to a medical professional. Based on the data, the medical professional can assess, diagnose, recommend and/or provide medical treatment, and/or communicate with the patient as necessary.

More specifically, apparatuses, systems and methods for wound management are described that provide for a patient to remotely capture an image of a wound, injury, lesion, cut, gash, sore, abrasion, laceration, or the like, and transmit the image to a medical professional for assessment. To assist in the assessment, a medical dressing and/or a temperature-indicating strip are applied to the wound prior to capturing the image. The medical dressing has a reference object that can provide a reference guide to assess swelling of an area around the wound. With the assistance of the reference object, the image of the medical dressing can be analyzed and used to diagnose an injury. The reference object includes markings that respond to movement of the underlying tissue. By measuring distances between the markings shown in the captured image, the image can be used to assess the healing of the underlying wound. The image capture device can collect and store images of wounds for later use. The temperature-indicating strip can provide a reference guide of the medical professional to assess a temperature around the wound and to assess fluid drainage from the wound. The systems and method for wound manage may be used on a variety of surgical wounds, such as but not limited to: plastic surgery wounds, ear, nose and throat (ENT) wounds (such as those involving the neck), all general surgery wounds (such as but not limited to those involving the abdomen), all gynecology wounds (such as but not limited to those affecting the abdomen), orthopedic wounds that do not involve the loss of tissues requiring vacuum assisted drainage (such as but not limited to knee replacement surgery and hip replacement surgery and vascular and heart surgical procedures that are performed through open skin incisions.

In other embodiments, apparatuses, systems and methods for monitoring swelling of a part of the human body are described herein. These systems and methods provide for a patient to remotely capture an image of the part of the body where a medical dressing has been applied (such as but not limited to a stocking or a compression stocking) and to transmit the image for processing and assessment. For assessment, the medical dressing conforms to the underlying tissue and includes a reference object that includes a plurality of markings. As the tissue underlying the markings swells or shrinks, distances between the markings on the medical dressing change. After the image is captured and transmitted to a processor for processing, the processor measures the distances between the markings and assesses if the swelling or shrinking is troublesome. These systems and methods may be used to assess a variety of medical conditions that require monitoring of swelling including but not limited to: chronic conditions such as but not limited to heart and kidney failure, where swelling of the lower limbs is common and often worsens with a decline in the underlying condition, and post-operative conditions such as but not limited to patients who have had limb surgery to monitor and inhibit deep venous thrombosis.

Dressing

Referring to FIG. 1, illustrated therein is a dressing 100 for applying to a wound according to one embodiment. Dressing 100 includes a membrane 102 and a plurality of containers 104.

Figure 2:
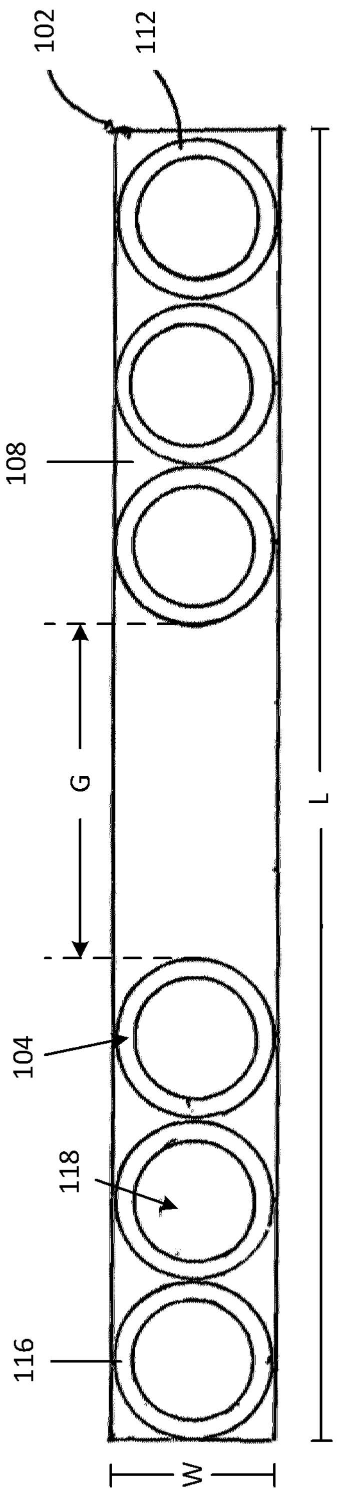
FIG. 2 is a bottom view of the dressing for applying to a wound of FIG. 1, accordingly to one embodiment.

Membrane 102 has a first side 106, a second side 108, a length L and a width W (see FIG. 2). Length L is preferably greater than width W such that membrane 102 has an elongated shape. Membrane 102 is made of a flexible material and is intended to stretch and expand in a direction along length L and/or in a direction along width W. In one embodiment, membrane 102 is made of a material that has a similar co-efficient of expansion as does normal skin of a human being. In this manner when the dressing 100 is applied to skin (as discussed below) across a wound and the skin in and around an area adjacent to the wound swells (e.g. due to edema under the wound), membrane 102 can provide for dressing 100 to stretch in a manner that mimics the stretching of the underlying epidermis during swelling. It should be noted that if membrane 102 did not expand, the adhesive material removably attaching the dressing to the epidermis could pull off (e.g. tear off) one or more superficial layers of the epidermis, thereby weakening the remaining layers of the epidermis and promoting the formation of blisters. For example, but not limited to, membrane 102 can be made of a material similar to Elastoplast.

Figure 3:
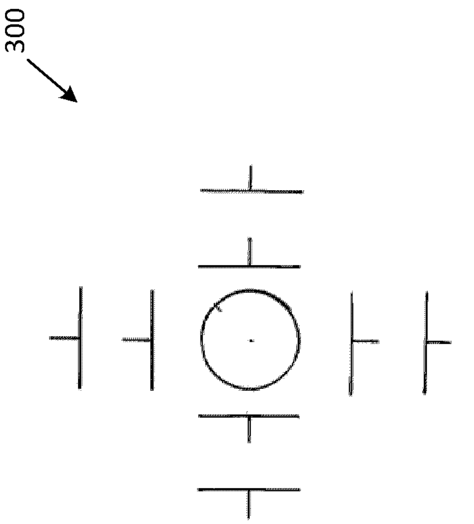
FIG. 3 is a top view of a reference object of the dressing for applying to a wound, according to one embodiment.
Figure 4:
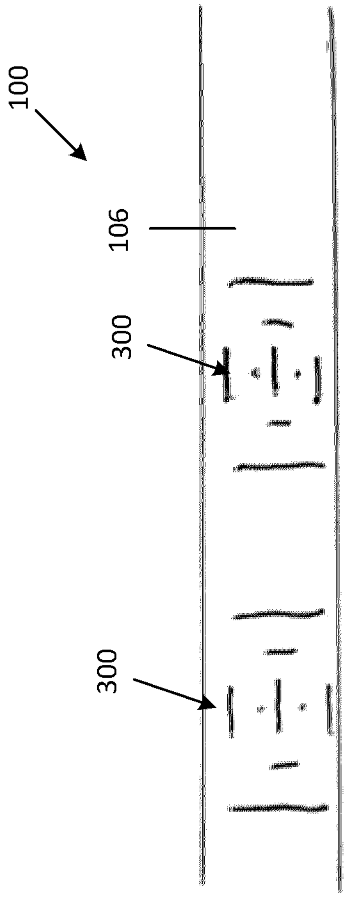
FIG. 4 is a top view of a dressing for applying to a wound of FIG. 1, accordingly to one embodiment.

Referring to FIGS. 3 and 4, in some embodiments of membrane 102, first side 106 of membrane 102 has at least one reference object 300 (see FIG. 3, below). Briefly, in one embodiment of a reference object, reference object 300 may provide a standardized outcome measure of expansion for a medical professional analyzing the wound. In one embodiment, reference object 300 has a series of vertical, horizontal and/or angular hairlines, dashes, etc. with known dimensions and/or spacing therebetween. After an image of the dressing is captured using the device, the application (e.g. a smartphone application) can compare dimensions of the reference object 300 (e.g. lengths of lines and/or symbols of the reference object, widths of lines and/or symbols of the reference object, spacing between lines and/or symbols of the reference object, etc.) in the image to stored dimensions of the reference object 300. Reference objects are further described with reference to FIG. 6.

In one specific embodiment, reference object 300 is based upon black bars embedded (e.g., but not limited to, stitched) within membrane 102 to provide for accurate measurement of longitudinal expansion along the membrane 102, both in terms of absolute length of membrane 102 and length of segments between adjacent containers 104, and similarly to provide for measurement of the width of the membrane (i.e. in two planes). For example, but not limited to, stretching of segments between adjacent containers 104 may be important to indicate wound swelling that is worse in one specific area of the wound, or worse close to the skin edge along the wound, such as if an infection is present.

Second side 108 of membrane 102 has at least one container 104 coupled thereto. Container 104 is sealingly coupled to membrane 102 at a first end 112. A second end 114 of container 104 is spaced apart from first end 112 by a continuous wall 116 defining a volume 118 of the container 104. The second end 114 defines an opening 120 to deliver contents stored in the volume 118 of the container 104 (see FIG. 5) to the wound when the dressing 100 is applied to the wound. Container 104 has a rigid continuous side wall 116 that can hold a material within volume 118. In one embodiment, wall 116 is made of a flexible material (e.g. a foam-based material). For example, but not limited to, wall 116 can be flexible to expand and contract in a direction of the planar membrane 102 coupled at their first end 112. In one embodiment, container 104 is round and has a cylinder-shape. Container 104 can have a diameter ranging from about 5 mm to 2 cm, depending on the specific wound system in which the dressing 100 is being used and/or the type of wound that the dressing 100 is being applied.

Figure 5:
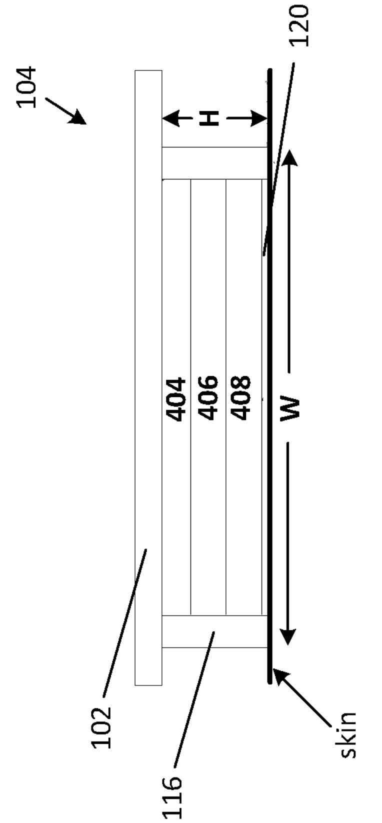
FIG. 5 is a side view of a container of the dressing for applying to a wound of FIG. 1, accordingly to one embodiment.

Referring to FIG. 5, the wall 116 of container 104 is maintained in an upright configuration (as shown in FIG. 5) by a pressure exerted on the wall 116 from internal medicaments 404, 406, 408 that can be delivered to the skin upon release from container 104. For example, but not limited to, container 104 can house medicaments 404, 406, 408 to be delivered to an area of skin adjacent to the wound of the patient. Medicaments 404, 406 and 408 can be different materials for applying to an area of skin around the wound for treatment of the wound. For example, but not limited to, medicament 404 can be a topical agent for pain relief, medicament 406 can be an anti-inflammatory drug and medicament 408 can be a soothing skin cream. The amount of and composition of medicaments 404, 406, 408 may reflect the current and future regulations governing medicaments 404, 406, 408. For example but not limited to, medicaments 404, 406, 408 may be available for purchase over-the-counter or may be prescribed by a physician. In one such example, Xylocaine may be included as one or medicaments 404, 406, 408 at various strengths; Xylocaine at a strength of 2.5% must be prescribed by a physician but Xylocaine at a strength of 0.2% may be purchased over the counter.

It should be noted that although FIG. 5 shows three layers of medicaments 404, 406, 408 being housed by container 104 to be delivered to the skin adjacent to the wound of the patient, more or less than three layers of medicaments can be housed by container 104.

As medicaments 404, 406, 408 exit the container 104 and are absorbed into the skin of the patient, an amount of medicaments held in container 104 decreases and the pressure exerted on the wall 116 by the materials 404, 406, 408 decreases. Accordingly, wall 116 may collapse as the materials 404, 406, 408 are released through opening 120 to allow the membrane 102 securing the first end 112 of the cylinders 104 to move closer to the skin (e.g. to decrease the height H of the container 104 (as shown in FIG. 2). The skin itself may swell, as noted above, and as the container 104 are removably attached to the skin at second end 114 of the container 104, walls 118 are flexible enough for the skin to deform those side walls in the direction of swelling, which is usually away from the wound.

The wall 116 of container 104 may have an attachment mechanism 122 removably attached to second end 114. Attachment mechanism 122 is shown in FIG. 1. Attachment mechanism 122 inhibits medicaments 404, 406, 408 from being released from volume 118 of container 104 prior to applying dressing 100 to a patient's wound. Upon removal of attachment mechanism 122 (as shown at 124 in FIG. 1) from dressing 102 prior to applying dressing 100 to a patient's wound, a fastening mechanism (not shown) may facilitate removable attachment of dressing 100 to the area of skin around the wound. For example, but not limited to, the fastening mechanism may be a glue such as but not limited to cyanoacrylate medical grade glues commonly available.

In one embodiment, medicaments 404, 406, 408 are layered within container 104 such that the medicament 404 is a gel containing a release formulation for an analgesic drug such as but not limited to Lignocaine or Marcaine, the medicament 406 is a gel containing an anti-inflammatory drug, and the medicament 408 is a soothing skin cream. In this configuration, each layer of medicaments 404, 406, 408 can be delivered to the area of skin around the wound in in a temporal sequence where the medicament 404 is delivered first, the medicament 406 is delivered next and the medicament 408 is delivered last.

In one embodiment, the medicament 404 and the medicament 406 can be separated by a boundary 410. Boundary 410 may be a dissolvable membrane, etc. depending on the constituent compounds of the medications and their known performance with respect to movement across the skin. The use of different medicaments from different purveyors of those medicaments may require a simple layering or the use of a dissolvable membrane.

In one embodiment, the medicament 406 and the medicament 408 can be separated by a boundary 412. Boundary 412 may be a dissolvable membrane, etc.

In another embodiment, container 104 can be filled with medicaments 404, 406, 408 which include proprietary analgesics, such as Buvivicaine and anti-inflammatory agents such as Diclofenac. Medicaments 404, 406, 408 can be gels or equivalent preparations that provide for an active ingredient to cross through the skin. As noted above, containers 104 can be temporarily sealed to retain medicaments 404, 406, 408 by an attachment mechanism 122 (e.g. a membrane) that can be removed by the applying medical profession when the wound is addressed for closure. Removal of attachment mechanism 122 may expose a ring of adhesive material. At present there are many known materials that are commercially available for removably attaching objects to the skin, including but not limited to cyanoacrylic agents in different formulations to prevent skin irritation or inflammation. Attachment mechanism 122 removably attaches the second end 114 of containers 104 to the skin.

A variable number of containers 104 can be present on dressing 100. For example, one or more containers 104 can be present. Generally, containers 104 are evenly spaced across membrane 102 while providing a gap G in a central portion of membrane 102. During application of dressing 100 to a person, gap G (see FIG. 1) should be aligned over the wound to prevent the dressing 100 from being removably attached at a position immediately adjacent to an edge of the wound (as removable attachment at a position immediately adjacent to an edge of the wound may lead to wound tearing upon removal of the dressing 100 from the skin).

Dressing 100 is configured to provide enough tension to hold the skin edges of the wound together. In one embodiment, positioning an equal number of containers 104 on either side of the wound applies equal tension across the wound. As noted above, the dimensions of dressing 100 and the number of containers 104 can be modified according to individual wounds by the medical professional.

The number of containers 104 of dressing 100 can depend on a size of the wound, a size of the dressing 100, the type of the wound, etc. The spacing of the containers 104 along membrane 102 can also depend on a size of the wound, a size of the dressing 100, the type of the wound, etc.

In one embodiment, the membrane 102 may be configured to expand between each container 104 and be rigid above each container 104. Containers 104 may be aligned along length L of membrane 102. Containers 10

In one embodiment, membrane 102 is sealingly coupled to cylinder 104, for example by a strong adhesive glue.

In one embodiment, membrane 102 can expand in the space between the containers (e.g. gap G (see FIG. 2), but the containers 104 do not expand but can deform, as the foam walls are not rigid. As the containers 104 empty of their contents the tendency of the containers to deform increases. Therefore, the containers 104 act to transmit the deformation caused by the swelling to the overlying membrane 102.

The deformation of membrane 102 is measured using an algorithm. Specifically, the algorithm measures the deformation of membrane 103 in two planes using a reference object or reference objects (e.g. reticules) on a top surface of membrane 102. An example reference object 600 is shown in FIGS. 6A-6C and further described below.

Reference object 600 can have various shapes and/or forms. For example, in one embodiment, the reference object 600 can be stitched into or attached (such as but not limited to by printing) to membrane 102 and comprise different shapes (e.g. a circle, vertical and/or horizontal lines, etc.) with defined physical dimensions when in an unstretched (e.g. neutral) configuration. As deformation of membrane 102 occurs (e.g. by swelling of the wound underlying membrane 102), changes in the dimensions of the shapes comprising the reference object (e.g. changes in the length, width and/or spacing between horizontal lines, vertical lines or circles) can be used to measure the swelling) of the underlying wound. For example, changes in the length and/or spacing between horizontal lines can indicate swelling in the vertical plane of the wound, whereas changes in the length and/or spacing of the vertical lines can indicate swelling in the horizontal plane. The changes in the physical dimensions of the reference object (e.g. changes in spacing, length and/or width of the lines and/or circles of the reference object) can be measured by an algorithm of a mobile application (as described further below) when an image of the reference object in a stretched configuration is captured on a smart phone.

Figure 6C:
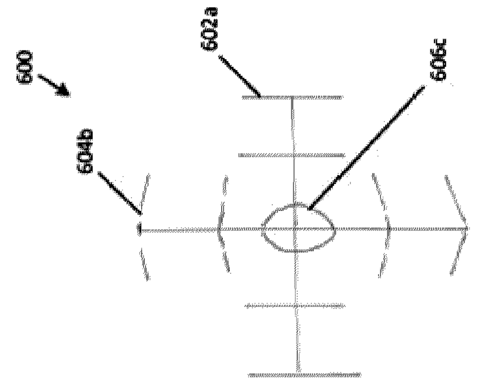
FIG. 6C is a top view of the reference object of FIG. 6A in a second stretched configuration, according to one embodiment.
Figure 6B:
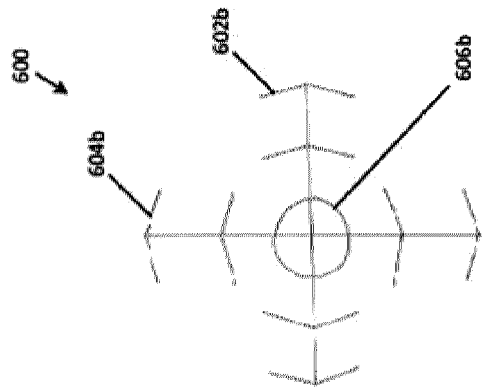
FIG. 6B is a top view of the reference object of FIG. 6A in a first stretched configuration, according to one embodiment.
Figure 6A:
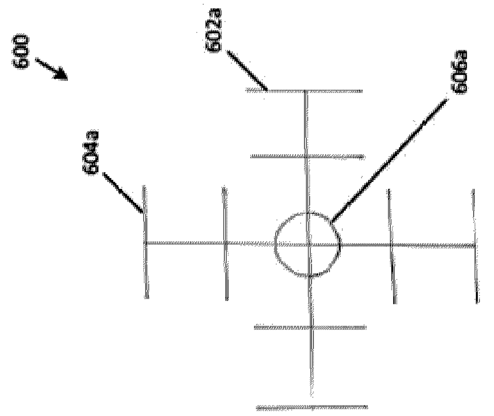
FIG. 6A is a top view of a reference object of the dressing for applying to a wound in a neutral configuration, according to one embodiment.

Referring now to FIGS. 6A-6C, illustrated therein are top views of another embodiment of a reference object. FIG. 6A shows reference object 600 comprising vertical lines 602*a*, horizontal lines 604*a* and a central portion 606*a* in a neutral configuration. FIG. 6B shows a first stretched configuration of reference object 600 where both vertical lines 602*b* and horizontal lines 604*b* have been stretched in at least two directions (e.g. the horizontal and the vertical direction) by deformation of the underlying elastic membrane 102. Further, central portion 606*b* has increased in size relative to central portion 606*a* due to deformation of the underlying elastic membrane 102. In FIG. 6C, vertical lines 602*a* remain unchanged relative to vertical lines 602*a* in FIG. 6A, however horizontal lines 604*b* are stretched due to deformation of the underlying elasticized membrane in one direction (e.g. in a direction perpendicular to the horizontal lines 604*a* in FIG. 1). In FIG. 6C, central portion 606*c* is stretched in one direction due to deformation of the underlying elasticized membrane in one direction (e.g. in a direction perpendicular to the horizontal lines 604*a* in FIG. 1).

In one embodiment, the central portion 606*a* of the reference object provides for measurement of deformation of one reference object relative to another reference object (e.g. of FIG. 6B relative to neutral configuration 6A), while the vertical and horizontal lines 602*a* and 604*a*, respectively, can be used to measure deformation within the reference object 600. This totality of measurement allows for wound monitoring both as a whole and according to each placed membrane 102, and within each membrane 102. This is designed to measure the expected deformation caused by swelling that is expected to be concentrated close to the skin wound, but if swelling were to occur outside of the normal for other parts of the wound, then this system would so identify that area and the degree of swelling.

In use, dressing 100 is intended to be placed across a wound (e.g. at a right angle to the wound). Membrane 102 is movable between a first position and a second position (e.g. is flexible/elastic) to provide for expansion of the membrane 102 with expansion of the underlying skin due to swelling in the area around the wound. In some embodiments, a reference object (e.g. reference object 300 or 600) on membrane 102 changes shape upon the expansion of membrane 102. As the wound expands due to normal healing, the reference objects 300, 600 on membrane 102 can be monitored with the application that uses a cell phone camera system to measure such expansion. The expansion co-efficient of membrane 102 can be calculated using a measuring algorithm, as described below, and can be sent to the attending medical professional with a time and date stamp. The medical professional may then assess the measured co-efficient of expansion of membrane 102 and relate the measured value to an expected outcome from knowledge or from a data base of similar wound types. If there is a significant deviation between the measured value and the expected outcome, then the medical professional can request a clinical examination of the patient, for example.

Preferably, the patient can capture images of the wound and dressing, or have images captured by a friend, relative, caregiver, etc. on a regular basis, and the medical professional can schedule appointments based on the observed results rather than routine or urgent based upon patient fears.

Figure 7:
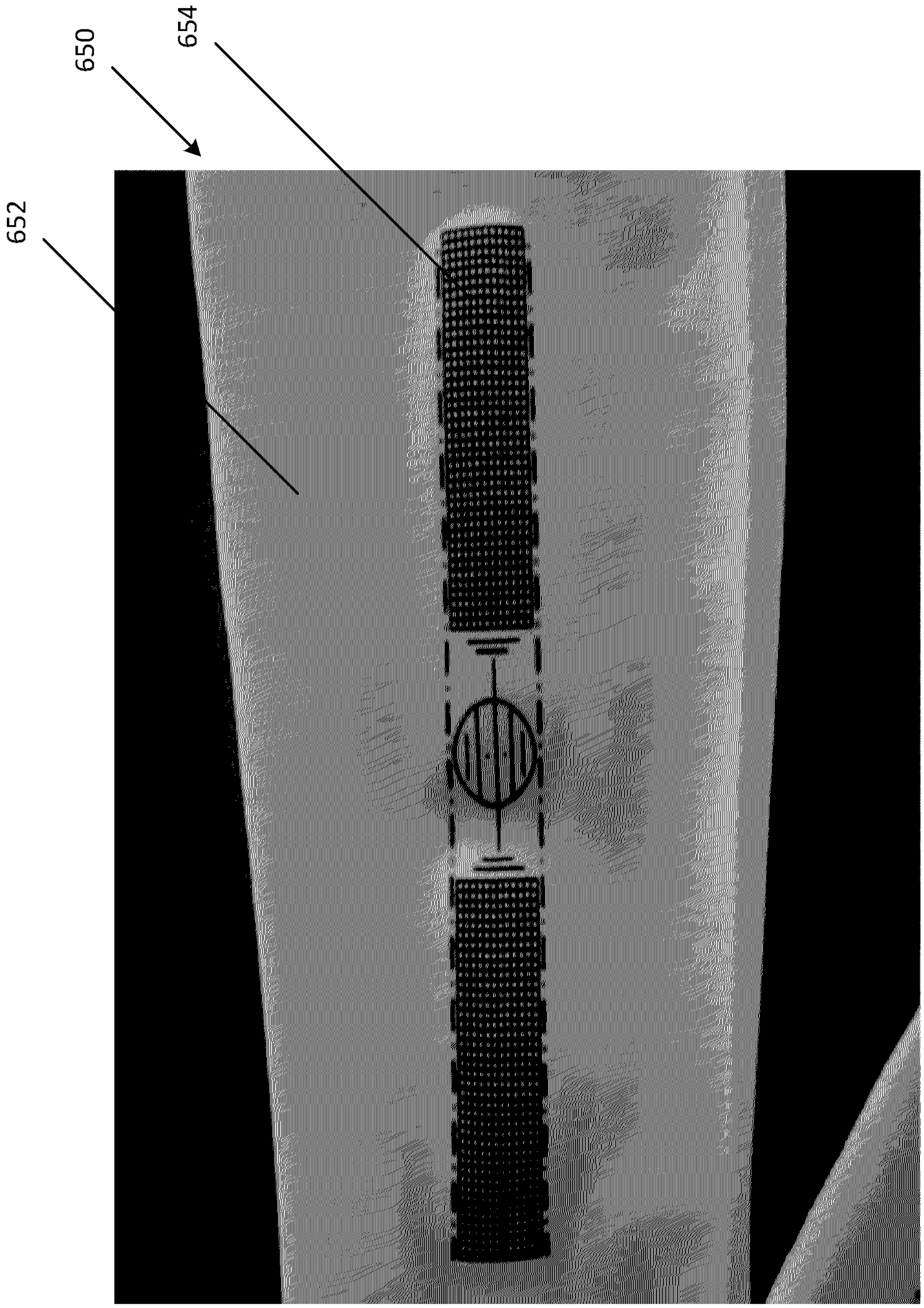
FIG. 7 is a top view of a system for monitoring swelling including a membrane and a reference object, according to one embodiment.
Figure 8:
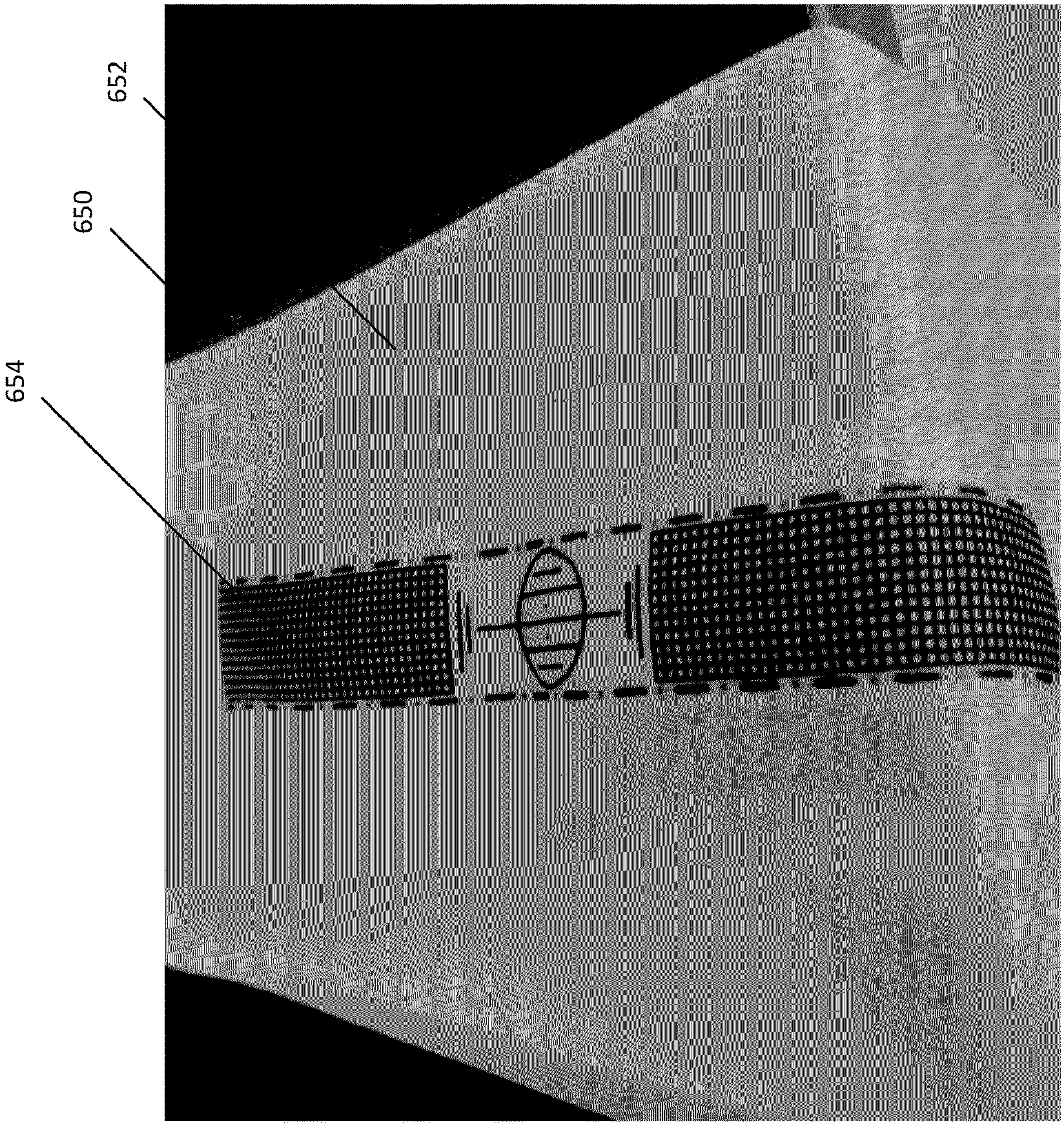
FIG. 8 is another top view of the system for monitoring swelling including a membrane and a reference object of FIG. 7.

Referring now to FIGS. 7 and 8, illustrated therein is another embodiment of a dressing 650 including a membrane 652 and a reference object 654. In this embodiment, dressing 650 can be applied to a part of a body to monitor swelling of the part of the body.

Figure 9:
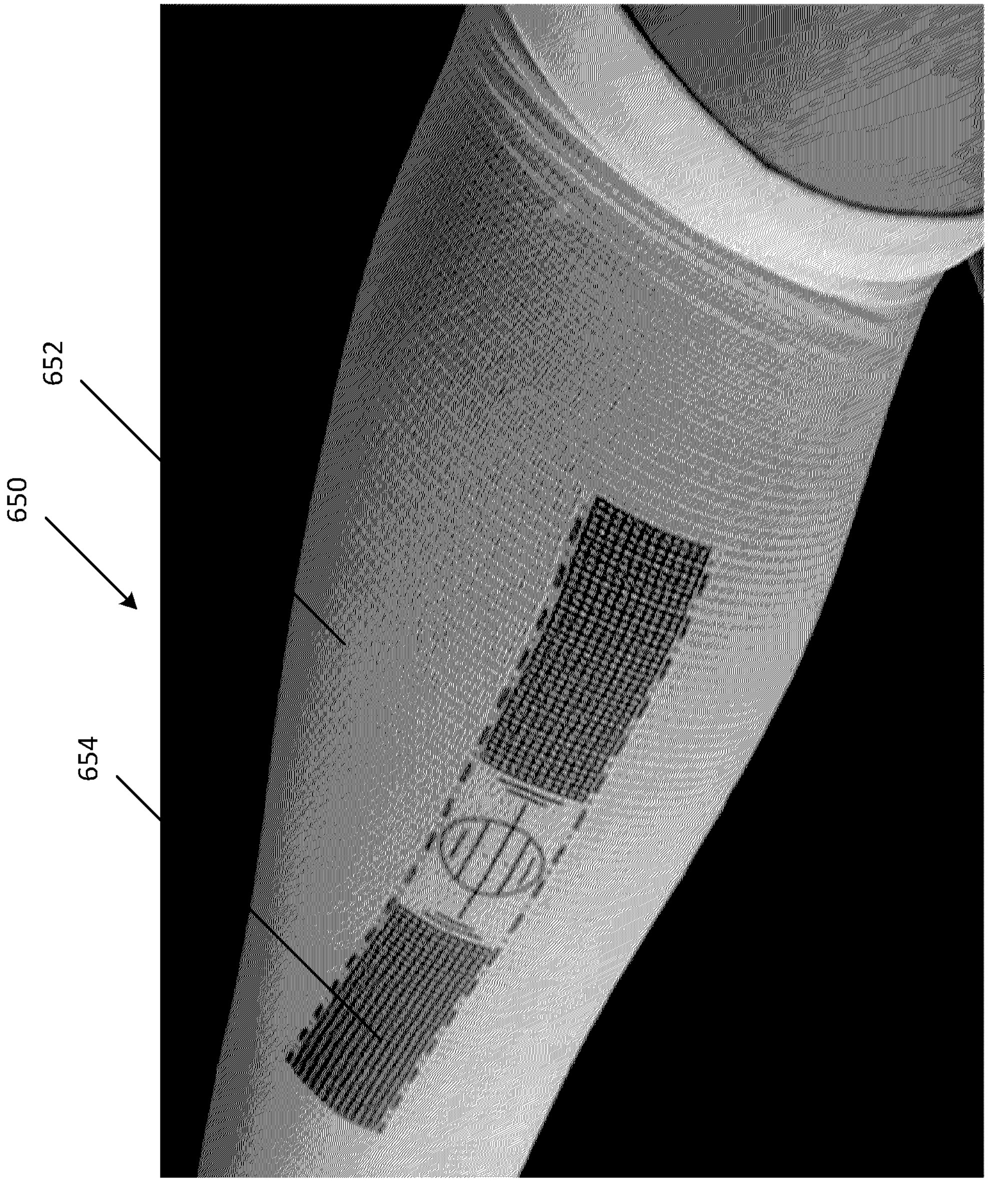
FIG. 9 is perspective view of the system for monitoring swelling including a membrane and a reference object of FIG. 7 shown worn on a limb.

Membrane 652 can be any membrane that, when applied to a part of a human body, conforms to the part of the human body. For instance, as shown in FIG. 9, dressing 650 may be a compression stocking that is worn on a limb (e.g. an arm or a leg) made of threads having an elastic core thread that is enwound with yarn containing cotton fibers.

Figure 10A:
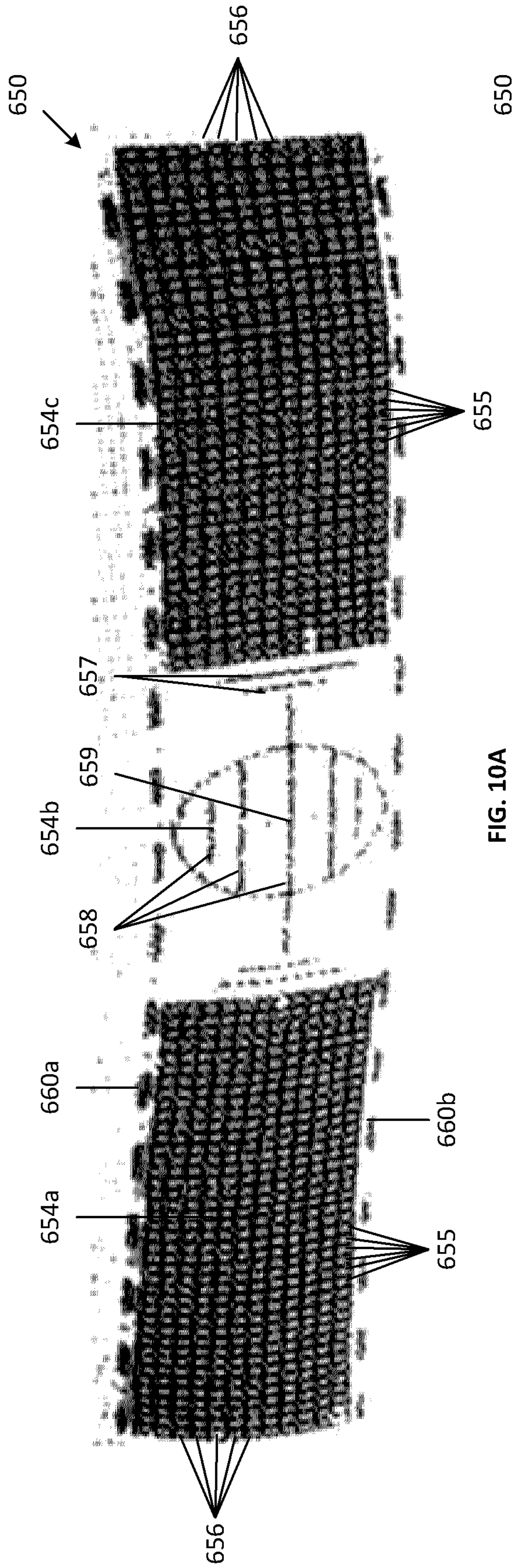
FIG. 10A is a top view of a schematic of the system for monitoring swelling including a membrane and a reference object of FIG. 7.
Figure 10B:
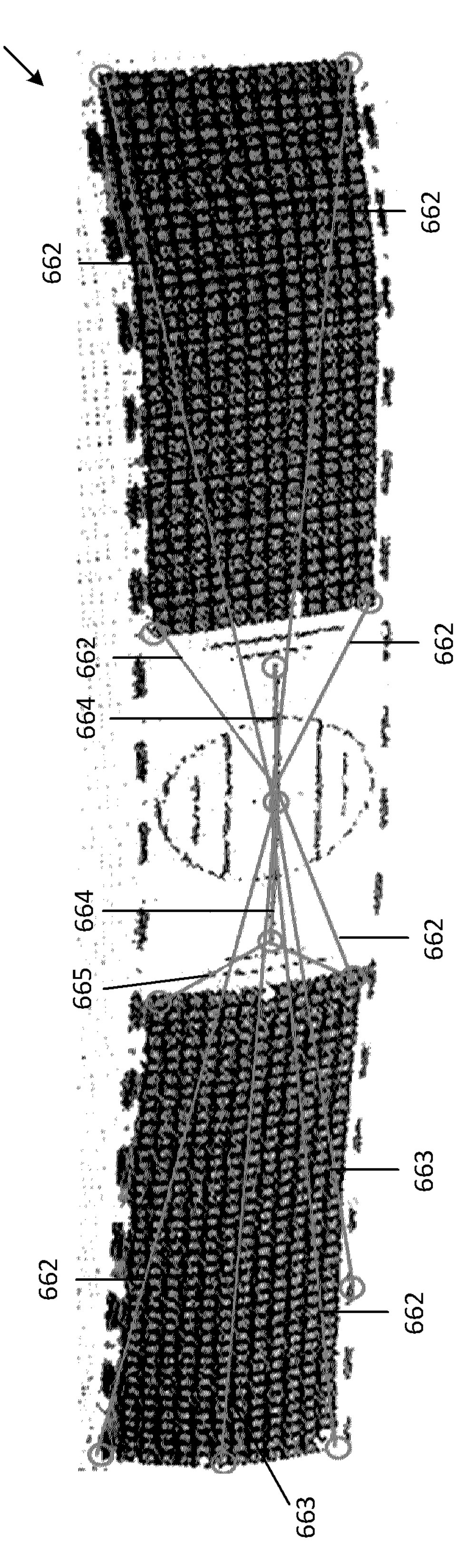
FIG. 10B is a top view of a schematic of the system for monitoring swelling including a membrane and a reference object of FIG. 7 showing various measurements for assessing swelling of tissue thereunder.

Reference object 654 can be applied to membrane 652 or be integral with membrane 652 and includes a plurality of markings. The markings can be an individual or a set of visual indicators that can be used to visualize changes in the shape of the dressing 650. Referring now to FIGS. 10A and 10B, the embodiment of dressing 650 shown therein includes three regions 654*a*, 654*b* and 654*c* of markings. Regions 654*a* and 654*c* each include a plurality of columns 655 and a plurality of rows 656 of markings to form a grid-like pattern having a rectangular shape. Region 654*b* includes vertical lines 657, horizontal lines 658 and a center point 659 and is shown positioned between the regions 654*a* and 654*c*.

Reference object 652 may also include a boundary line 660, which may be a solid line or a dashed line, indicating a boundary of the reference object 654. In the embodiment shown in FIGS. 10A and 10B, the boundary line 660 includes an upper dashed line 660*a* and a lower dashed line 660*b* as well as outer end points of each of the rows 656.

As shown in FIG. 10B, measurements between a variety of features of the reference object 652 can be made to analyze the movement of tissue underlying the membrane 652. In one example, measurements can be made between any of the corners of the regions 654*a* and 654*c* and center point 659. Examples of these measurements are indicated by lines 662 in FIG. 10B. In another example, measurements can be made between any of the portions of the boundary lines 660*a* and 660*b* and center point 659. Examples of these types of measurements are indicated by lines 663 in FIG. 10B. In another example, measurements can be made between any of the end points of the vertical lines 657 and horizontal lines 658 and center point 659. Examples of these types of measurements are indicated by lines 664 in FIG. 10B. In another example, measurements can be made between any of the corners of the regions 654*a* and 654*c* and end points of the vertical lines 657 and horizontal lines 658. An example of this type of measurement is indicated by line 665 in FIG. 10B.

As deformation of membrane 652 occurs (e.g. by swelling or shrinking of the tissue underlying the dressing 650), changes in the markings of reference object 654 (e.g. changes in the length, width and/or spacing between horizontal lines, vertical lines or circles and/or changes of distance between various points on the markings, as described above) can be used to measure the swelling and/or shrinking of the underlying tissue. The changes in the physical dimensions of the reference can be captured in an image and transmitted to a processor for analysis.

Figure 11:
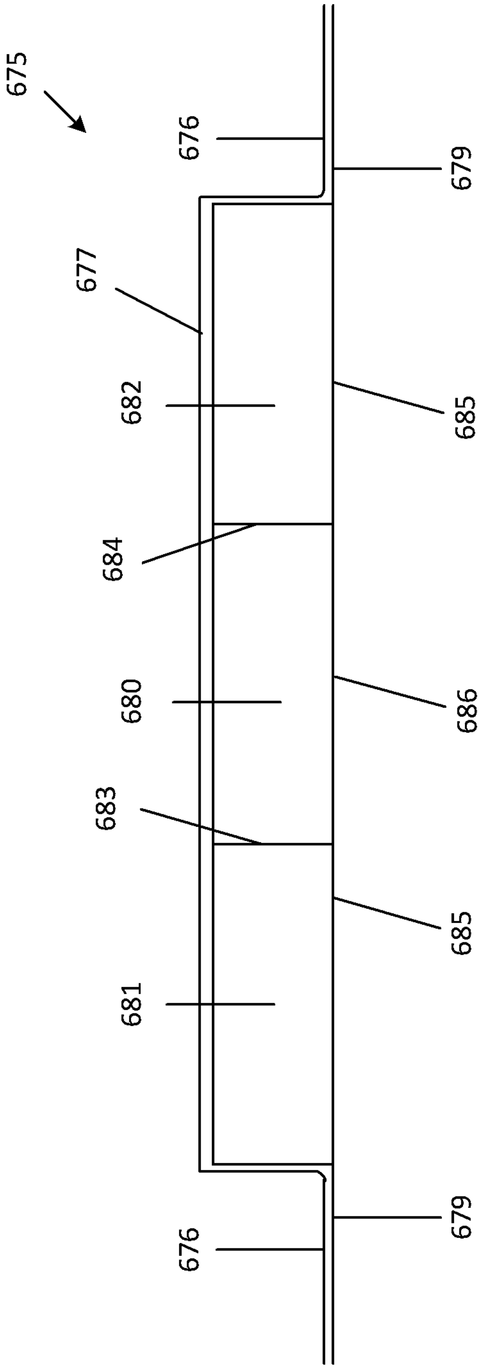
FIG. 11 is a side view of a dressing for collecting fluid from a wound, according to one embodiment.

A cross-sectional image of another embodiment of a dressing 675 is shown in FIG. 11. Dressing 675 includes an elastic membrane 676 and a reticule 677 printed on a top surface of the elastic membrane 676. Dressing 675 also includes a collection chamber 680 positioned between two medicament chambers 681, 682. Medicament chamber 681, 682 can be filled with a medicament to be applied to a wound when the dressing 675 covers or substantially covers a wound, as previously described with respect to FIG. 1. Medicament chambers 681, 682 may be separated from collection chamber 680 by rigid sidewalls 683, 684, that inhibit transfer of fluid between the medicament chambers 681, 682 and the collection chamber 680. Rigid sidewalls 683, 684 may have similar properties to the side wall 116 described above. A first base 685 covers a bottom portion of each of the medicament chambers 681, 682 and controls the delivery of the medicament from the medicament chambers 681, 682 to the wound. A second base 686 may be included to cover a bottom portion of the collection chamber 680. In some embodiments, second base 686 may encourage the absorption of fluid from the wound into the collection chamber 680. in some embodiments, second base 686 may encourage fluid in collection chamber 680 to be retained in collection chamber 680. The dressing 675 may be removably secured to tissue using an adhesive disposed on a bottom surface 679 of at least a portion of the elastic membrane 676.

In some embodiments, the dressings described herein may include a holograph that has been applied to a top surface of the dressing that changes between a first configuration when the elastic membrane is in a natural state and a second configuration when the elastic membrane has been stretched. The holograph may be used to indicate a manufacturer of the dressing.

Temperature-Indicating Strip

Figure 12A:
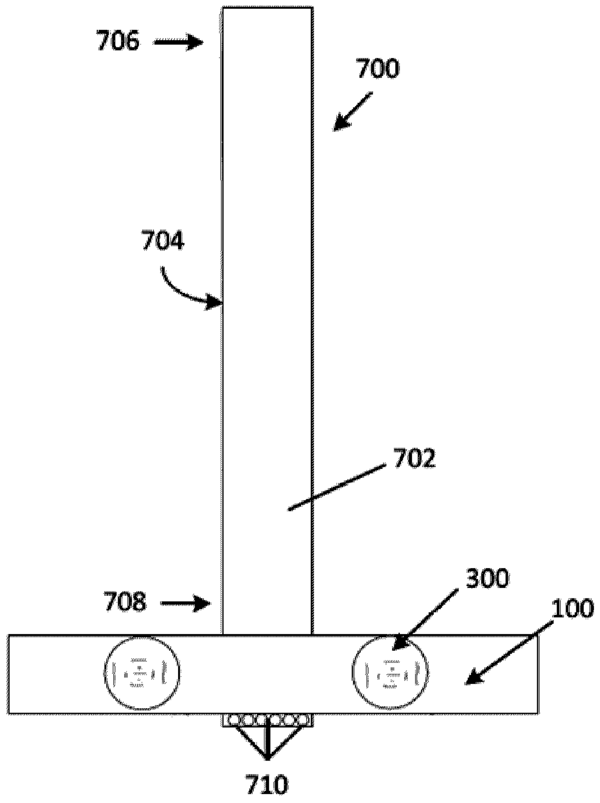
FIG. 12A is a top view of a system for monitoring wound healing including the dressing for applying to a wound of FIG. 1 and a temperature-indicating strip, according to one embodiment.
Figure 12B:
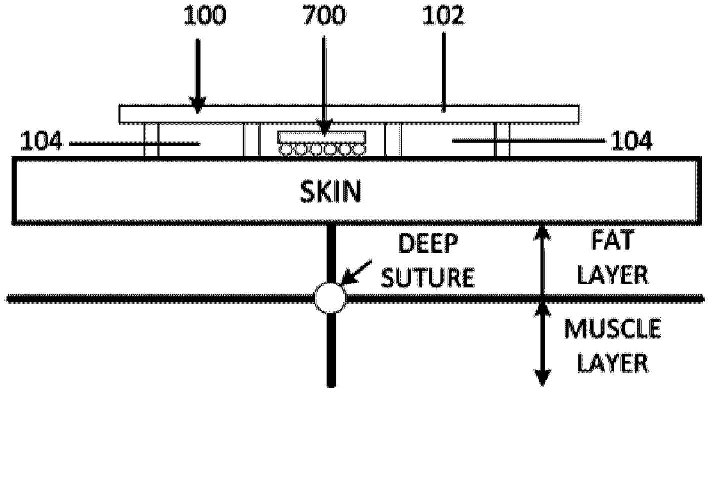
FIG. 12B is a side view of a system for monitoring wound healing including the dressing for applying to a wound of FIG. 1 and a temperature-indicating strip, according to one embodiment.

Referring to FIGS. 12A and 12B, illustrated therein is a temperature-indicating strip 700. The temperature-indicating strip 700 has a first side 702, a second side 704, a first end 706 and a second end 708.

The temperature-indicating strip 700 generally is applied longitudinally along a wound and is a separate apparatus from the dressing 100 described above.

Temperature-indicating strip 700 is applied to a placed system which collects fluid discharge from the wound via a plurality of tubes 710. Tubes 710 are separate from 700 and are coupled (e.g. glued) to the skin on either side of the wound, with proprietary bioglues, such as but not limited to cyanoacrylic-based bioglues, the tubes 710 being separate from the temperature sensing device 700, and being sterile when applied to the wound. The application of the sterile tube 710 seals the wound and provides for the application of the non-sterile (e.g. alcohol cleaned), temperature sensing strip 700 to be applied over and to either side of the tube 710 system. Tubes 710 are so coupled to second side 704 of temperature-indicating strip 700 in the operating room by the surgeon. Tubes 710 are configured to receive fluid discharged from the wound and direct the fluid towards one of ends 702 and 704. In one embodiment, tubes 710 can couple to a collection device (not shown) that collects the fluid from tubes 710 (e.g. thereby forming a closed system with temperature-indicating strip 700). The fluid collected from the wound into tubes 710 can be blood, body fluids, infectious discharge or the like. A closed system of collection has obvious advantages to the patient and medical professional.

As shown in FIGS. 12A and 12B, when used in conjunction with a dressing 100 as described herein, temperature-indicating strip 700 is generally positioned below dressing 100 longitudinally along and directly over the wound. Dressings 100 can then be applied over the temperature-indicating strip 700 (e.g. at right angles) to measure an amount of swelling of the area around the wound.

In one embodiment, the discharge is collected by tubes 710 by capillary forces through linear capillary channels in the tubes 710 (not shown), directed trough the tubes 710 by capillary forces and absorbed into an absorbent material of a collecting vessel (not shown).

Temperature-indicating strip 700 may provide a medical professional with direct data when used in conjunction with the dressing 100. For example, upon capturing an image of dressing 100 and temperature-indicating strip 700, temperature-indicating strip 700 will indicate a temperature of the wound by exhibiting a distinct physical appearance (e.g. a distinct colour on first side 702).

In one embodiment, temperature-indicating strip 700 is made of plastic-based material that can change colours according to the ambient temperature of skin to which it is attached. In one example, a temperature range of the temperature-indicating strip 700 may be between 36° C. and 40° C.

For example, in some embodiments the temperature-indicating strip may comprise liquid crystals that change colour with changes in temperature of underlying surfaces. These liquid crystals may be Thermochromic Liquid Crystals (TLCs), Cholesteric Liquid Crystals, or the like. In some embodiments, the liquid crystals may be micro-encapsulated for protection, stabilization and to make the liquid crystals easier to use.

In some embodiments, the temperature-indicating strip is a FeverScan™ temperature-indicating strip (by LCRHallcrest, Glenview, IL).

Wound Measurement Application

One or more systems described herein may be implemented in computer programs executing on programmable computers, each comprising at least one processor, a data storage system (including volatile and non-volatile memory and/or storage elements), at least one input device, and at least one output device. For example, and without limitation, the programmable computer may be a programmable logic unit, a mainframe computer, server, and personal computer, cloud based program or system, laptop, personal data assistance, cellular telephone, smartphone, or tablet device.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device readable by a general or special purpose programmable computer for configuring and operating the computer when the storage media or device is read by the computer to perform the procedures described herein.

A description of an embodiment with several components in communication with each other does not imply that all such components are required. On the contrary a variety of optional components are described to illustrate the wide variety of possible embodiments of the present invention.

Further, although process steps, method steps, algorithms or the like may be described (in the disclosure and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical. Further, some steps may be performed simultaneously.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

Figure 13:
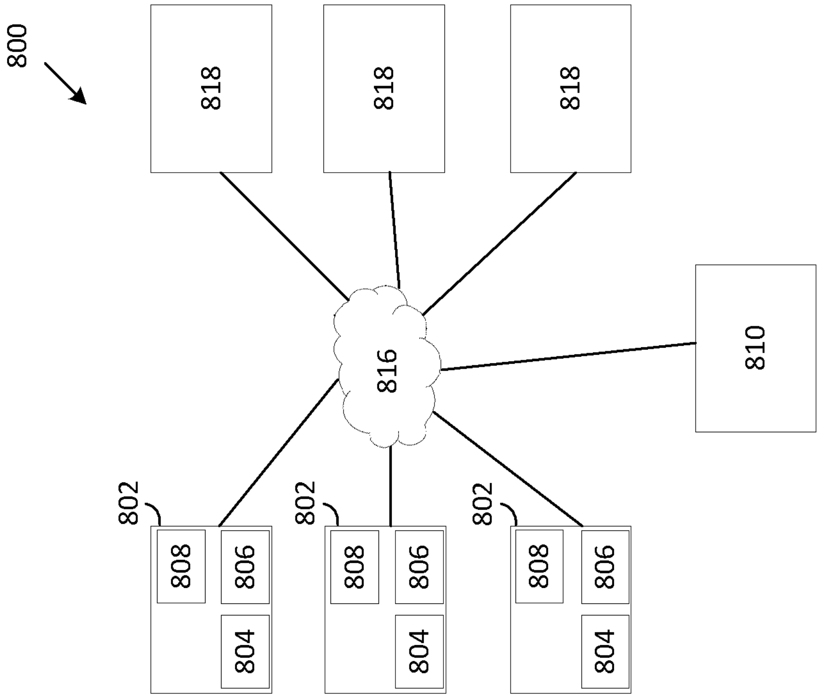
FIG. 13 is a block diagram illustrating a wound management system for monitoring wound healing according to one embodiment.

FIG. 13 shows a block diagram illustrating a wound management system 800 for monitoring wound healing, in accordance with an embodiment. The wound management system 800 is for monitoring wound healing by measuring and detecting differences exhibited by multiple devices (e.g. the dressing 100 and the temperature-indicating strip 700, as previously described). The wound management system 800 is not restricted to a single wound, but may be extended to multiple wounds of the same type and/or different types, each including multiple devices.

The management system 800 provides for medical professionals (e.g. physicians, surgeons, nurses, etc.) to measure and monitor wound healing of a patient without having to physically see the patient in person. To accomplish this, the wound management system 800 comprises a plurality of patient devices 802, each having a camera 804, and a processor 806. For example, a patient having a wound can take a picture of the wound using their mobile device 802 with a mobile application 808 stored thereon. The patient can use the mobile application 808 to send the picture to server 810 for redistribution to a physician device 818 for assessment. Medical professional device 818 can send information back to server 810 or directly to mobile device 802.

The server 810 communicates with the plurality of patient devices 802, a plurality of physician devices 818 via a network 816. The server 810 may be a purpose built machine designed specifically for implementing a system and method for creating maps of a facility.

The server 810, patient devices 802 and physician devices 818 may be a server computer, desktop computer, notebook computer, tablet, PDA, smartphone, or another computing device. The devices 802, 810 and 818 may include a connection with the network 816 such as a wired or wireless connection to the Internet. In some cases, the network 816 may include other types of computer or telecommunication networks. The devices 802, 810 and 818 may include one or more of a memory, a secondary storage device, a processor, an input device, a display device, and an output device. Memory may include random access memory (RAM) or similar types of memory. Also, memory may store one or more applications for execution by processor. Applications may correspond with software modules comprising computer executable instructions to perform processing for the functions described below. Secondary storage device may include a hard disk drive, floppy disk drive, CD drive, DVD drive, Blu-ray drive, or other types of non-volatile data storage. Processor may execute applications, computer readable instructions or programs. The applications, computer readable instructions or programs may be stored in memory or in secondary storage, or may be received from the Internet or other network 20. Input device may include any device for entering information into device 802, 810 and 818. For example, input device may be a keyboard, keypad, cursor-control device, touch-screen, camera, or microphone. Display device may include any type of device for presenting visual information. For example, display device may be a computer monitor, a flat-screen display, a projector or a display panel. Output device may include any type of device for presenting a hard copy of information, such as a printer for example. Output device may also include other types of output devices such as speakers, for example. In some cases, devices 802, 806, 810, 814 may include multiple of any one or more of processors, applications, software modules, second storage devices, network connections, input devices, output devices, and display devices.

Although devices 802, 810 and 818 are described with various components, one skilled in the art will appreciate that the devices 802, 810 and 818 may in some cases contain fewer, additional or different components. In addition, although aspects of an implementation of the devices 802, 810 and 818 may be described as being stored in memory, one skilled in the art will appreciate that these aspects can also be stored on or read from other types of computer program products or computer-readable media, such as secondary storage devices, including hard disks, floppy disks, CDs, or DVDs; a carrier wave from the Internet or other network; or other forms of RAM or ROM. The computer-readable media may include instructions for controlling the devices 802, 810 and 818 and/or processor to perform a particular method.

In the description that follows, devices such as server 810, patient devices 802 and physician devices 818 are described performing certain acts. It will be appreciated that any one or more of these devices may perform an act automatically or in response to an interaction by a user of that device. That is, the user of the device may manipulate one or more input devices (e.g. a touchscreen, a mouse, or a button) causing the device to perform the described act. In many cases, this aspect may not be described below, but it will be understood.

As an example, it is described below that the devices 802 and 818 may send information to the server 810. For example, a patient user may manipulate one or more input devices (e.g. a mouse and a keyboard) to interact with a user interface displayed on a display of the patient device 802. Generally, the patient device 802 may receive a user interface from the network 816 (e.g. in the form of a webpage). Alternatively or in addition, a user interface may be stored locally at a patient device 802 (e.g. a cache of a webpage or a mobile application).

Server 810 may be configured to receive a plurality of information, from each of the plurality of patient devices 802 and physician devices 810. Generally, the information may comprise at least an identifier identifying the patient or physician, respectively. For example, the information may comprise one or more of a username, e-mail address, password, or social media handle. The server may also receive an image of a wound and the devices 100, 700 described above for a physician to assess healing of the wound.

In response to receiving information, the server 810 may store the information in a storage database. The storage database may correspond with secondary storage of the devices 802, 818. Generally, the storage database may be any suitable storage device such as a hard disk drive, a solid state drive, a memory card, or a disk (e.g. CD, DVD, or Blu-ray etc.). Also, the storage database may be locally connected with server 806. In some cases, the storage database may be located remotely from server 806 and accessible to server 806 across a network for example. In some cases, storage database may comprise one or more storage devices located at a networked cloud storage provider.

The patient device 802 may be associated with a patient account. Similarly, the physician device 818 may be associated with a facility account. Any suitable mechanism for associating a device with an account is expressly contemplated. In some cases, a device may be associated with an account by sending credentials (e.g. a cookie, login, or password etc.) to the server 810. The server 810 may verify the credentials (e.g. determine that the received password matches a password associated with the account). If a device is associated with an account, the server 806 may consider further acts by that device to be associated with that account.

The devices 802, 818 and the server 810 may communicate asynchronously, for example, by using an implementation of the WebSocket protocol, such as Socket.IO. Updates may be sent from the server 810 to each of the devices 802, 814 in real time as interrupts, i.e., without polling. Likewise, user interaction data may be sent from each of the devices 802, 818 to the server 810 in real time as interrupts, i.e., without polling.

Figure 14:
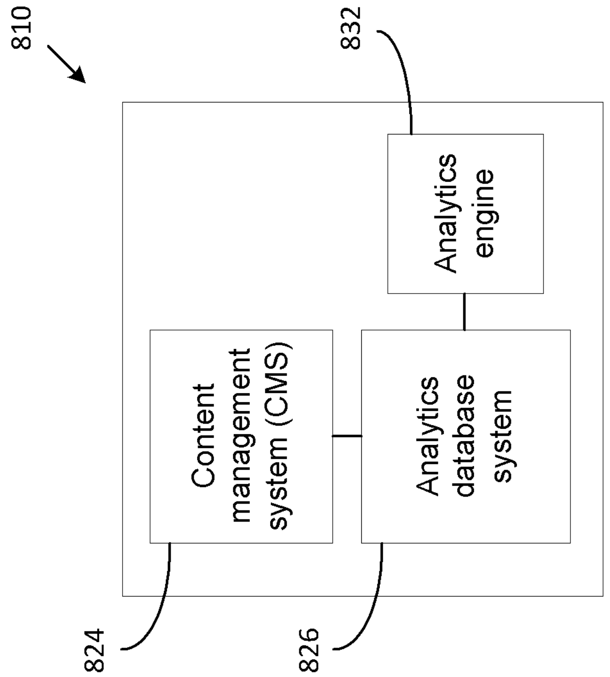
FIG. 14 is a block diagram of a server platform of the wound management system of FIG. 13, accordingly to one embodiment.

Turning now to FIG. 14, illustrated therein is the server 810, in accordance with an embodiment. The server 810 includes a content management system (CMS) 824, and an analytics database system 826. The server 810 may include multiple backend devices, e.g., servers. The CMS 824 and the analytics database system 826 may be hosted by the server 810.

In some embodiments, the CMS 824 may be a frontend interface application, typically, implemented as a web service. In some embodiments, CMS 824 stores content, including information relating to the wound images, handles updates to the content received from the devices 802, 818 and provides content to the devices 802, 818. For example, the CMS 824 may be a no structured query language (NoSQL) database application.

In some embodiments, the analytics database system 826 includes or is operatively connected to an analytics engine 832. The analytics database system 826 may be a database application, typically implemented as a web service. The analytics database system 826 stores all user interactions, e.g., user selections or "hits", searches, dates, types of mobile device, and generates analytics relating to the user interactions. Advantageously, because user interactions are recorded for several different devices of the devices 802, 818, a relatively large sample size is obtained. Further, the analytics database system 826, with analytics engine 832, performs and stores aggregate data analysis on the collective data set that can allow for analysis of wound specific data sets, institutional wound outcome, individual surgeon and provider outcomes and any other appropriate opportunities for analysis of different types of wound treatment options.

In some embodiments, the application 808, when launched on the patient device 802, takes control of the camera 804. In some embodiments, an identity of the patient is confirmed prior to launching the application. For example, the application 808 can confirm the identity of the patient using one or more of facial recognition software, an iris scan or a fingerprint scan on the mobile device 802. Confirmation information generated based on one of the aforementioned techniques of confirming an identity can be recorded and linked to the medical record at server 810. Confirmation can occur when the application 808 has been downloaded into mobile device 802. In another example, a physician can provide confirmation information through physician device 818 such as by entering a license number, for example. Physician confirmation information cannot be viewed or retrieved by the patient and but resides on server 810.

When application 808 is launched and camera 804 is focused on the wound, application 808 assumes control by the camera 804 through recognition of, for example, specific markers of reference object 300 of membrane 102. The application 808 can then project an azimuth onto a display of the mobile device 802 which can guide the holder of the device 802 to align the camera 804 with the wound to the most optimal position to get a representative picture of the wound.

In one embodiment, application 808 can optimize a view of dressing 100 and/or temperature-indicating strip 700 using reference bar codes (not shown) embedded in edges of the membrane 102 and strip 700, respectively. In one example, the reference bar codes can describe a type of wound that is being dressed and/or other manufacturing data.

Application 808 can use the reference object 300, for example embedded into the surface of membrane 102, to both guide the device 102 as to positioning and to measure expansion (i.e. stretching) of membrane 102 due to wound swelling. When applied to a wound, membrane 102 traverses the wound (e.g. extends across the wound). Accordingly, by positioning multiple reference objects 300 along membrane 102, expansion (i.e. stretching) can be measured along the length L of dressing 100, which may be particularly important for large wounds such as abdominal wounds.

In another embodiment, the patient is able to control who has access to the image date transferred via application 808, so that various medical professionals can have access to the image data. Access to data can be configured at server 806 where the image data is stored. In some embodiments, image data is may not be stored on the device 102. Rather, a patient can request to receive image data stored on server 806 for a period of time after providing the image data to server 806 (e.g. for a period of 2 years after the service is used).

The combination of measurement of skin expansion and skin temperature can provide significant feedback for a medical professional. It should be noted that application 806 is also capable of measuring the expansion of membrane 102 as a whole and the expansion of membrane 102 between the containers 104. Application 806 can record image data, measurement data, etc. and display changes over time (e.g. changes in measurement data) as additional images are captured of the same wound, thereby providing real-time changes to the medical professional.

Figure 15:
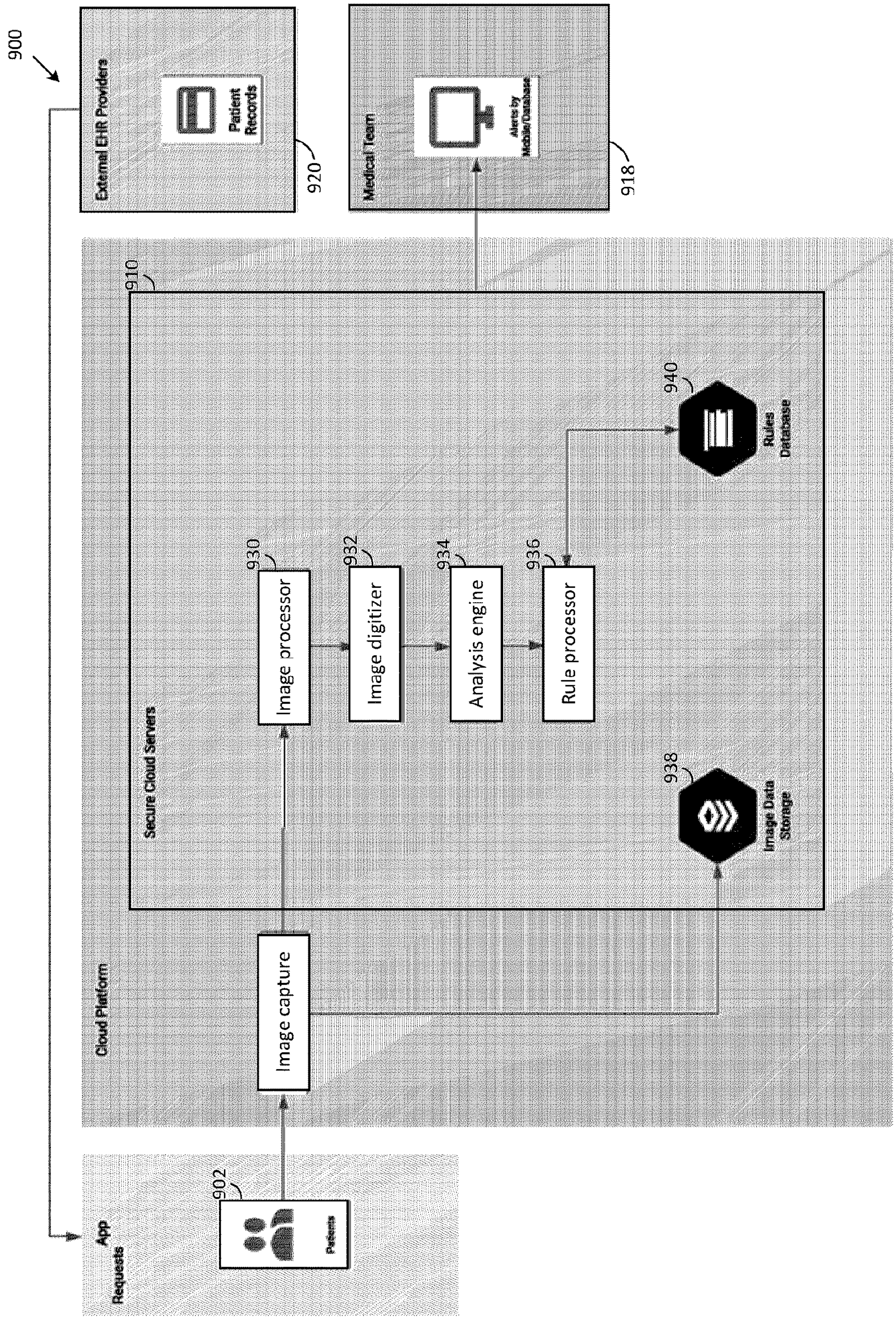
FIG. 15 is a block diagram of a system for monitoring swelling, according to one embodiment.

FIG. 15 shows another diagram illustrating a system 900 for monitoring swelling, in accordance with another embodiment. The system 900 is for monitoring wound healing by measuring and detecting differences between features of a reference object on a dressing.

System 900 includes at least one patient device 902, at least one server 910 and at least one physician device 918. Patient device 902 captures an image of a dressing (e.g. dressing 650) and transmits the image (e.g. over a network) to the server 910. The image is received by an image processor 930 of the server 910. An image digitizer 932 receives the images from the processor 930 and transforms the image into a set of digital values. Once the image has been transformed to a set of digital values, it is analyzed using the analysis engine 934 which performs and stores aggregate data analysis on the collective data. The rule processor 936 applies various rules to the digital image to assess deformation of the dressing and therefore swelling of the underlying tissue.

Examples

Wound Management System

The Wound Management Application may collect hundreds of data points with each image captured for a particular wound care application. For example, on day 1 of healing, initial points of the reference object covering the wound may be captured by converting the image to x, y coordinates on a Cartesian plane. On day 2, and several subsequent days thereafter, a new image may captured and the values of the x, y co-ordinates of the reference object may be mapped to new x, y coordinates. The application can calculate the difference between each corresponding point, as delta x (dx), and delta y (dy) values. Each point is matched with a previous day's point by using a unique 'origin image', to establish the relative location of each point, and thus, the corresponding delta value.

As each wound will heal differently (e.g. based on the location of the wound on the body and surgical procedure performed, as well as other factors), the proposed algorithm may have different "modes" for analyzing wounds. For example, an abdominal wound for appendix removal may be mapped against similar wounds to track the healing process of the wound.

Further, it should be noted that each measurement point on the reference object may be unique and identified accurately from a center point of the reference object. Differences between each point on the reference object can be measured in 1/100 of a millimeter, and can be represented by positive or negative values on the user interface (for example), based on the direction of change on a Cartesian plane.

In the initial stages of machine learning, the wound management application may be populated with normal and healthy cases, to identify expected outcomes for a healthy patient. Upon implementation, the wound management application may identify abnormal healing based on the algorithm established.

An exemplary data table showing changes in position of a plurality of data points A1, A2, A3, . . . , A100 for a patient is shown below:

| POINT-ID | DX | DY | DATE&TIME |
|---|---|---|---|
| A1 | +1 mm | +2 mm | 2017 Aug. 20 11:00 |
| A2 | +1 mm | +2 mm | 2017 Aug. 20 11:00 |
| A3 | +1 mm | +2 mm | 2017 Aug. 20 11:00 |
| . . . | | | |
| A100 | +1 mm | +2 mm | 2017 Aug. 20 11:00 |

Using exponential decay regression, for example, the wound management application may determine and/or predict whether a wound is healing normally or abnormally and may automatically generate an alert for a physician (e.g. the surgeon) providing details of the wound and or healing process (e.g. a likelihood of infection). In one example, the likelihood of infection of A normal wound healing regression over time generally will approach zero, whereas other abnormal wound healing regressions do not. Moreover, wound healing regressions can also be used to predict the time for normal healing to be achieved by converting the exponential function to a parametric equation where dx, and dy are dependent over time.

While the above description provides examples of one or more apparatus, methods, or systems, it will be appreciated that other apparatus, methods, or systems may be within the scope of the claims as interpreted by one of skill in the art.

What is claimed is:

1. A system for monitoring wound closure, the system comprising:

a dressing for applying to the wound, the dressing comprising:

an elasticized membrane having a first side and a second side;

a reference object disposed on the first side of the elasticized membrane, the reference object comprising a plurality of markings that respond to movement of underlying tissue when the dressing is applied to the wound, the plurality of markings including one or more line markings and one or more point markings; and an adhesive disposed on at least a portion of the second side of the elasticized membrane to adhere the elasticized membrane to an area of skin around the wound;

wherein, when the dressing is applied to the wound, in response to the movement of the underlying tissue, the elasticized membrane moves between a relaxed state where the plurality of markings of the reference object have a first shape and a stretched state where the plurality of markings of the reference object have a second shape, the second shape being different than the first shape; and wherein, the second shape being different than the first shape indicates a first change in a first physical dimension between a first pair of markings of the plurality of markings that indicates deformation of the elasticized membrane in a first direction and a second change in a second physical dimension between a second pair of markings of the plurality of markings that indicates deformation of the elasticized membrane in a second direction, the deformation of the elasticized membrane being caused by swelling of the underlying tissue;

a camera for capturing an image of the plurality of markings of the reference object when the plurality of markings have the second shape; and a processor configured to:

compare the second shape of the plurality of markings from the image to the first shape of the plurality of markings from a stored image and measure the first change between the first pair of markings indicating deformation of the elasticized membrane in the first direction and the second change between the second pair of markings indicating deformation of the elasticized membrane in the second direction; and based on measuring the first change and the second change, determine a degree of swelling of the underlying tissue by:

generating measurement data from the measured first change and second change;

comparing the measurement data to previous measurement data from one or more previously captured images of the same wound; and identifying when the measurement data indicates swelling outside of a normal healing progression.

2. The system of claim 1, wherein the processor is remotely located and the camera further comprises a transmitter for transmitting the image to the processor over a network.

3. The system of claim 1, wherein the camera and the processor are part of a computing device.

4. The system of claim 1, wherein the dressing further comprises at least one container coupled to the second side of the elasticized membrane, the at least one container having a first end sealingly coupled to the elasticized membrane, a second end spaced from the first end defining an opening of the container, and a continuous wall between the first end and the second end defining a volume of the container.

5. The system of claim 1, wherein the reference object is a reticule and a second region includes a series of horizontal lines for indicating deformation of the elasticized membrane in the first direction and a series of vertical lines for indicating deformation of the elasticized membrane in the second direction.

6. A system for monitoring wound closure, the system comprising:

a computer processor coupled to a memory, wherein the computer processor is programmed to monitor closure of the wound by:

receiving from a patient device image data representative of second shape of a plurality of markings of a reference object disposed on an elasticized membrane of a dressing applied to the wound, the dressing having an adhesive to adhere the dressing to an area of skin around the wound, the plurality of markings being responsive to movement of underlying tissue, the elasticized membrane moving between a relaxed state where the plurality of markings have a first shape and a stretched state where the plurality of markings have a second shape, the second shape being different than the first shape;

comparing the second shape of the plurality of markings from the image to the first shape of the plurality of markings from a stored image;

measuring a first change in a physical dimension between a first pair of markings indicating deformation of the elasticized membrane in a first direction and a second change in a physical dimension between a second pair of markings indicating deformation of the elasticized membrane in a second direction;

based on measuring the first change and the second change, determining a degree of swelling of the underlying tissue by:

generating measurement data from the measured first change and second change;

comparing the measurement data to previous measurement data from one or more previously captured images of the same wound; and identifying when the measurement data indicates swelling outside of a normal healing progression; and transmitting the degree of swelling and the image data to a physician device for assessment.

7. The system of claim 1, wherein the dressing is a stocking or a compression stocking.

8. The system of claim 6, wherein the dressing is a stocking or a compression stocking.

* * * * *